(12) United States Patent
Haught et al.

(10) Patent No.: US 9,884,130 B2
(45) Date of Patent: Feb. 6, 2018

(54) COMPOSITIONS FOR DELIVERY OF ORAL COMFORT SENSATIONS

(71) Applicant: The Procter & Gamble Company, Cincinnati, OH (US)

(72) Inventors: John Christian Haught, West Chester, OH (US); Kotikanyadanam Tatachar Sreekrishna, Mason, OH (US); Yakang Lin, Liberty Township, OH (US)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 0 days.

(21) Appl. No.: 14/539,357

(22) Filed: Nov. 12, 2014

(65) Prior Publication Data

US 2015/0297753 A1 Oct. 22, 2015

Related U.S. Application Data

(60) Provisional application No. 61/903,579, filed on Nov. 13, 2013.

(51) Int. Cl.

| | | |
|---|---|---|
| *A61K 49/00* | (2006.01) | |
| *A61K 9/70* | (2006.01) | |
| *A61K 31/047* | (2006.01) | |
| *A61K 31/365* | (2006.01) | |
| *A61K 31/11* | (2006.01) | |
| *A61K 31/20* | (2006.01) | |
| *A61K 33/00* | (2006.01) | |
| *A61K 31/05* | (2006.01) | |
| *A61K 36/534* | (2006.01) | |
| *A61K 36/185* | (2006.01) | |
| *A61K 8/33* | (2006.01) | |
| *A61K 8/34* | (2006.01) | |
| *A61K 8/37* | (2006.01) | |
| *A61Q 11/00* | (2006.01) | |
| *A61K 8/36* | (2006.01) | |
| *A61K 8/43* | (2006.01) | |
| *A61K 8/55* | (2006.01) | |
| *A61K 8/66* | (2006.01) | |

(52) U.S. Cl.
CPC ............ *A61K 49/0004* (2013.01); *A61K 8/33* (2013.01); *A61K 8/347* (2013.01); *A61K 8/361* (2013.01); *A61K 8/37* (2013.01); *A61K 8/375* (2013.01); *A61K 8/43* (2013.01); *A61K 8/55* (2013.01); *A61K 8/66* (2013.01); *A61K 9/7007* (2013.01); *A61K 31/047* (2013.01); *A61K 31/05* (2013.01); *A61K 31/11* (2013.01); *A61K 31/20* (2013.01); *A61K 31/365* (2013.01); *A61K 33/00* (2013.01); *A61K 36/185* (2013.01); *A61K 36/534* (2013.01); *A61Q 11/00* (2013.01); *A61K 2800/782* (2013.01)

(58) Field of Classification Search
CPC . A61K 8/361; A61K 8/43; A61K 8/55; A61K 8/66; A61K 2800/782; A61K 49/0004; A61K 9/7007; A61K 31/047; A61K 31/365; A61K 31/11; A61K 31/20; A61K 33/00; A61K 31/05; A61K 36/534; A61K 36/185; A61K 8/33; A61K 8/375; A61Q 11/00

See application file for complete search history.

(56) References Cited

U.S. PATENT DOCUMENTS

| | | |
|---|---|---|
| 2,946,725 A | 7/1960 | Norris et al. |
| 3,070,510 A | 12/1962 | Cooley et al. |
| 3,111,127 A | 11/1963 | Jarboe |
| 3,535,421 A | 10/1970 | Briner et al. |
| 3,538,230 A | 11/1970 | Pader et al. |
| 3,862,307 A | 1/1975 | Di Giulio et al. |
| 3,917,613 A | 11/1975 | Humbert et al. |
| 3,991,178 A | 11/1976 | Humbert et al. |
| 4,029,759 A | 6/1977 | Humbert et al. |
| 4,051,234 A | 9/1977 | Gieske et al. |
| 4,070,496 A | 1/1978 | Rowsell et al. |
| 4,136,163 A | 1/1979 | Rowsell et al. |
| 4,150,052 A | 4/1979 | Watson et al. |
| 4,153,679 A | 5/1979 | Rowsell et al. |
| 4,157,384 A | 6/1979 | Browning et al. |
| 4,178,459 A | 12/1979 | Rowsell et al. |
| 4,206,215 A | 6/1980 | Bailey |
| 4,230,688 A | 10/1980 | Rowsell et al. |
| 4,340,583 A | 7/1982 | Wason |
| 4,459,425 A | 7/1984 | Amano et al. |
| 5,004,597 A | 4/1991 | Majeti et al. |
| 5,180,577 A | 1/1993 | Polefka et al. |
| 5,266,592 A | 11/1993 | Grueb et al. |
| 5,281,410 A | 1/1994 | Lukacovic et al. |
| 5,451,404 A | 9/1995 | Furman |

(Continued)

FOREIGN PATENT DOCUMENTS

| | | |
|---|---|---|
| DE | 19730651 | 1/1999 |
| EP | 310299 | 4/1989 |

(Continued)

OTHER PUBLICATIONS

International Search Report with Written Opinion dated Mar. 4, 2015, 7 pages.
Alistair Mathie, Kathryn A. Rees, Mickael F. El Hachmane and Emma L. Veale; Trafficking Of Neuronal Two Pore Domain Potassium Channels; Current Neuropharmacology, Sep. 2010; 8(3): 276-286.
Edmund M. Talley, Guillermo Solorzano, Qiubo Lei, Donghee Kim, and Douglas A. Bayliss; CNS Distribution Of Members Of The Two-Pore-Domain (KCNK) Potassium Channel Family; The Journal of Neuroscience, 2001 21(19):7491-7505.
Michel Fink, Fabrice Duprat, Florian Lesage, Roberto Reyes, Georges Romey, Catherine Heurteaux and Michel Lazdunskil; Cloning, Functional Expression and Brain Localization Of A Novel Unconventional Outward Rectifier K+ Channel; The EMBO Journal vol. 15 No. 24 pp. 6854-6862, 1996.

(Continued)

*Primary Examiner* — Robert Cabral (57) ABSTRACT

TREK-1 agonist comprising composition that reduces perceived oral discomfort sensation and a method for measuring TREK-1 potassium channel activation.

12 Claims, 1 Drawing Sheet

(56) References Cited

U.S. PATENT DOCUMENTS

| | | | |
|---|---|---|---|
| 5,578,293 | A | 11/1996 | Prencipe et al. |
| 5,589,160 | A | 12/1996 | Rice |
| 5,603,920 | A | 2/1997 | Rice |
| 5,608,119 | A | 3/1997 | Amano et al. |
| 5,651,958 | A | 7/1997 | Rice |
| 5,658,553 | A | 8/1997 | Rice |
| 5,703,123 | A | 12/1997 | Pelzer et al. |
| 5,716,601 | A | 2/1998 | Rice |
| 5,725,865 | A | 3/1998 | Mane et al. |
| 5,843,466 | A | 12/1998 | Mane et al. |
| 5,977,166 | A | 11/1999 | Greenberg |
| 6,242,217 | B1 | 6/2001 | Meadows et al. |
| 6,365,215 | B1 | 4/2002 | Grainger et al. |
| 6,451,844 | B1 | 9/2002 | Watkins et al. |
| 6,592,884 | B2 | 7/2003 | Hofmann et al. |
| 6,884,903 | B2 | 4/2005 | Lorenz et al. |
| 6,956,139 | B2 | 10/2005 | Green et al. |
| 7,112,403 | B1* | 9/2006 | Patel ............ G01N 33/5041 435/3 |
| 7,189,760 | B2 | 3/2007 | Erman et al. |
| 7,625,562 | B2 | 12/2009 | El Haj et al. |
| 2010/0003330 | A1* | 1/2010 | Baker, Jr. ............ A61K 8/062 424/489 |
| 2010/0330002 | A1* | 12/2010 | Robinson ............ A61K 8/64 424/48 |
| 2015/0118166 | A1* | 4/2015 | Sagel ............ A61K 8/362 424/49 |

FOREIGN PATENT DOCUMENTS

| | | |
|---|---|---|
| EP | 1187627 B1 | 9/2003 |
| WO | WO2005049553 | 6/2005 |
| WO | WO2006066334 | 6/2006 |
| WO | WO2006103401 | 10/2006 |

OTHER PUBLICATIONS

Florian Lesage, Eric Guillemare, Michel Fink, Fabrice Duprat, Michel Lazdunski, Georges Romey and Jacques Barhanin; TWIK-1, A Ubiquitous Human Weakly Inward Rectifying K+ Channel With A Novel Structure; The EMBO Journal vol. 15 No. 5 pp. 1004-1011, 1996.

Roberto Reyes, Fabrice Duprat, Florian Lesage, Michel Fink, Miguel Salinas, Nicolette Farman, and Michel Lazdunski; Cloning and Expression of a Novel pH-sensitive Two Pore Domain K1 Channel from Human Kidney; The Journal of Biological Chemistry (1998) vol. 273, No. 47, pp. 30863-30869.

\* cited by examiner

SEQUENCE LISTING

```
<160> NUMBER OF SEQ ID NOS: 1

<210> SEQ ID NO 1
<211> LENGTH: 1122
<212> TYPE: DNA
<213> ORGANISM: Mus musculus

<400> SEQUENCE: 1
atgggtgcag tggcggcccc tgacttgctg gatcccaagt ctgctgctca gaactccaaa      60
ccgaggctct cattctcctc aaaacccacc gtgcttgctt cccgggtgga gagtgactcg     120
gccattaatg ttatgaaatg gaagacagtc tccacgattt tcctggtggt cgtcctctac     180
ctgatcatcg gagccacggt gttcaaggca ttggagcagc ctcaggagat ttcccagagg     240
accaccattg tgatccagaa gcagaccttc atagcccagc atgcctgcgt caactccacc     300
gagctggacg aactcatcca gcaaatagtg gcagcaataa acgcagggat tatcccctta     360
ggaaacagct ccaatcaagt tagtcactgg gacctcggaa gctctttctt ctttgctggt     420
actgttatca caaccatagg atttgaaac atctccccac gaactgaagg tgaaaaata      480 ttctgcatca tctatgcctt gctgggaatt cccctctttg gctttctact ggctggggtt     540
```

-continued

```
ggtgatcagc taggaactat atttggaaaa ggaattgcca aagtggaaga cacatttatt    600
aagtggaatg ttagtcagac gaagattcgt atcatctcca ccatcatctt catcctgttt    660
ggctgtgtcc tctttgtggc tctccctgcg gtcatattca agcacataga aggctggagc    720
gccctggacg ctatctattt tgtggttatc actctgacga ccattggatt tggagactac    780
gtggcaggtg gatcagacat tgaatatctg gacttctaca agcctgtggt gtggttctgg    840
atcctcgttg ggctggccta ctttgcagct gttctgagca tgattgggga ctggctacgg    900
gtgatctcta agaagacgaa ggaagaggtg ggagagttca gagcgcatgc cgctgagtgg    960
acagccaatg tcacggccga gttcaaggaa acgaggaggc ggctgagcgt ggagatctac   1020
gacaagttcc agcgtgccac atccgtgaag cggaagctct ccgcagagct ggcgggcaac   1080
cacaaccagg aactgactcc gtgtaggagg accctgtctt ag                      1122
```

COMPOSITIONS FOR DELIVERY OF ORAL COMFORT SENSATIONS

FIELD OF THE INVENTION

The present invention relates to a TREK-1 agonist comprising composition that reduces perceived oral discomfort sensation.

BACKGROUND OF THE INVENTION

A family of potassium selective ion channels, including four transmembrane domain, dual pore domain potassium (K+) channels (4T/2P)—TWIK, TREK, TASK-1, TASK-2 and TRAAK—are involved in the control of background membrane conductance associated with various potassium driven sensory responses, such as anti-pain (*Curr Neuropharmacol.* 2010 September; 8(3): 276-286). These channels are interesting targets for consumer products aiming to deliver anti-pain/irritation or provide overall comfort benefits. Within this group, TWIK-1, TREK-1, TASK-1 and TASK-2 are widely distributed in many different tissues, while TRAAK is present exclusively in brain, spinal cord and retina (*The Journal of Neuroscience*, 2001 21(19):7491-7505). The 4T/2P channels have different physiologic properties; TREK-1 channels, are outwardly rectifying (Fink et al. (1996) EMBO J 15(24):6854-62), while TWIK-1 channels, are inwardly rectifying (Lesage et al. (1996) EMBO J 15(5):1004-11. TASK channels are regulated by changes in pH while TRAAK channels are stimulated by arachidonic acid (Reyes et al. (1998) JBC 273(47):30863-30869).

Members of the two-pore family of K+ channels have a variety of properties, ranging from acid-sensitivity to anesthetic sensitivity. TREK-1, TREK-2, and TRAAK are members of the two-pore family that are activated by a variety of conditions, including membrane stretch, pH, cell swelling, shear stress or negative pressure.

K+ channels are involved in multiple different processes and are important regulators of homeostasis in nearly all cell types. Their relevance to consumer product interaction with the consumer and their role in many human diseases, suggests that consumer products could be designed to target specific channel subtypes. Agonists to these channels have yet to see use in pharmaceutical applications, as the presently available channel agonists tend to be non-specific and elicit both positive and negative responses, thereby reducing clinical efficacy. Other agonists to two-pore-domain K+ channel family members that may be used in consumer products include agonists to: TASK-1 (KCNK3), TASK-2 (KCNK5), TASK-3 (KCNK9), TREK-1 (KCNK2), TREK-2 (KCNK10), TRAAK (KCNK4), and TWIK-1 (KCNK1)—alternative nomenclature in parenthesis.

The sensation of cold or heat depends on the activation of specific nerve endings in the skin. This involves heat- and cold-sensitive excitatory transient receptor potential (TRP) receptors, modulated by a thermal or chemical signal mostly via calcium ion channels. In an analogous manner, the mechano-gated and highly temperature-sensitive potassium channels of the TREK/TRAAK family, which normally work as silencers of the excitatory channels, are also implicated in the role of sensory receptors. They are important for the definition of temperature thresholds and temperature ranges in which excitation of nociceptor takes place and for the intensity of excitation when it occurs. TRAAK and TREK-1 channels are expressed with thermo-TRP channels in sensory neurons, and control pain produced by mechanical stimulation and both heat and cold pain perception in mice. Expression of TRAAK alone or in association with TREK-1 controls heat responses of both capsaicin-sensitive and capsaicin-insensitive sensory neurons. Together TREK-1 and TRAAK channels are important regulators of nociceptor activation by cold, particularly in the nociceptor population that is not activated by menthol. The TREK-1 channel has been linked to the TRPV1 pain response and has been reported as co-expressed for this type of pain signal.

In U.S. Pat. No. 6,242,217, Glaxo disclosed the gene sequence for the human TREK-1 polypeptide.

In EP 1187627B1, agonists and antagonists to the TREK-1 channel were applied to the treatment of epilepsy, sleep-related disorders, the induction of sleep, cognitive dysfunction/enhancement, attention deficit disorder, addiction, anxiety/phobia, dyskinesias including Parkinson's, Huntington's chorea, Cerebral palsy, incontinence, erectile dysfunction, or alopecia.

In U.S. Pat. No. 7,625,562B2, the University of Keele disclosed an in vitro method for the generation of cartilage tissue from mammalian chondrocyte progenitor cells expressing mechanosensitive TWIK-related potassium (TREK) ion channels.

In WO 2006/066334A1, Adelaide Research & Innovation disclosed a method of modulating cardiac rhythm in a human subject, the method including the step of modulating the activity of TREK-1 and/or TREK-2 in the heart of the subject.

Although the TREK-1 potassium channel has been reported to be highly expressed in the brain, ovary and small intestine (WO 2006/066334A1), it has not been reported to be active in driving comfort response to a stimulus. None of the afore mentioned art disclosed the application of the TREK-1 potassium channel, its agonists or antagonists, for consumer product application. What is needed are TREK-1 agonists that can be used in products to positively influence consumer perception of the products and methods of determining TREK-1 agonist effectiveness.

SUMMARY OF THE INVENTION

A personal care composition is provided that comprises a TREK-1 agonist.

A method for measuring TREK-1 potassium channel activation is provided that comprises providing oral care composition having greater than about 0.005% TREK-1 agonists; applying pain stimuli to oral tissues; treating oral tissues with oral care composition; and measuring the reduction in perceived pain.

DETAILED DESCRIPTION OF THE INVENTION

It has now surprisingly been found that agonists to the TREK-1 potassium channel (TREK-1) drive positive consumer perception from products containing them. The TREK-1 agonists further drive enhanced reduction in tooth sensitivity and/or oral discomfort, thus providing an oral comfort sensation. The present invention relates to compositions comprising one or more TREK-1 agonists and a process for measuring the TREK-1 efficacy of compositions containing >0.005% TREK-1 agonists and/or compositions containing traditional pain reducing and debriding agents comprising potassium salts, such as potassium nitrate or potassium oxalate, stannous fluoride, salicyl alcohol, benzocaine, dylclonine hydrochloride, hexylresorcinol, menthol, alum, zinc chloride, elm bark, gelatin, glycerin, pectin, carbamide peroxide, hydrogen peroxide, sodium bicarbonate, or sodium perborate. The process for measuring the TREK-1 efficacy of compositions includes the steps of: applying pain stimuli to oral tissues, treating with a composition containing a TREK-1 agonist, such treatment can comprise application of a flexible and/or soluble strip for a period of time, and measuring the reduction in perceived pain. The methods to ascertain the level of tooth sensitivity can be obtained by two primary methods: (1) Cold method—Blow air on a tooth or use a piece of ice on the sensitive area; and (2) Pressure method—place firm pressure on different sides of the tooth using an instrument or fingers to determine if sensitivity is present. In order to determine if a TREK-1 agonist containing composition (TREK-1 composition) is efficacious, the technology may be delivered to the affected site via a dentifrice, mouthwash, floss, denture adhesive, or tooth strip. Optionally, the TREK-1 composition could be placed on a physical device, such as floss or a strip and delivered to the site of sensitivity. The level of sensitivity reduction would then be measured.

Without being limited by theory, it is now believed that agonists of the TREK-1 potassium channel positively influence the consumer's perception of induced pain and/or irritation from activities in their daily routine. Activities such as eating or drinking hot or cold beverages, shaving, wearing deodorant, encounters with environmental pollutants, brushing teeth, flossing teeth, can benefit from the comfort sensations provided by the TREK-1 receptor agonists.

All percentages and ratios used hereinafter are by weight of total composition, unless otherwise indicated. All percentages, ratios, and levels of ingredients referred to herein are based on the actual amount of the ingredient, and do not include solvents, fillers, or other materials with which the ingredient may be combined as a commercially available product, unless otherwise indicated.

All measurements referred to herein are made at 25° C. (i.e. room temperature), unless otherwise specified.

As used herein, the word "include," and its variants, are intended to be non-limiting, such that recitation of items in a list is not to the exclusion of other like items that may also be useful in the materials, compositions, devices, and methods of this invention.

As used herein, the word "or" when used as a connector of two or more elements is meant to include the elements individually and in combination; for example X or Y, means X or Y or both.

By "personal care composition" is meant a product which in the ordinary course of usage is applied to or contacted with a body surface to provide a beneficial effect. Body surface includes skin, for example dermal or mucosal; body surface also includes structures associated with the body surface for example hair, teeth, or nails. Examples of personal care compositions include a product applied to a human body for improving appearance, cleansing, odor control or general aesthetics. Non-limiting examples of personal care compositions include hair coloring compositions; oral care compositions; after shave gels and creams; pre-shave preparations; shaving gels; creams, or foams; moisturizers and lotions; cough and cold compositions; leave-on skin lotions and creams; shampoos; conditioners; shower gels; bar soaps; toilet bars; antiperspirants; deodorants; depilatories; lipsticks; foundations; mascara; sunless tanners; and sunscreen lotions.

By "oral care composition", as used herein, is meant a product, which in the ordinary course of usage, is not intentionally swallowed for purposes of systemic administration of particular therapeutic agents, but is rather retained in the oral cavity for a time sufficient to contact dental surfaces or oral tissues. Examples of oral care compositions include dentifrice; mouth rinse; mousse; foam; mouth spray; lozenge; chewable tablet; chewing gum; oral care strips, such as tooth whitening strips, breath freshening dissolvable strips, or sensitivity strips; floss and floss coating; or denture care or adhesive product. The oral care composition may also be incorporated onto strips or films for direct application or attachment to oral surfaces.

Figure 1:
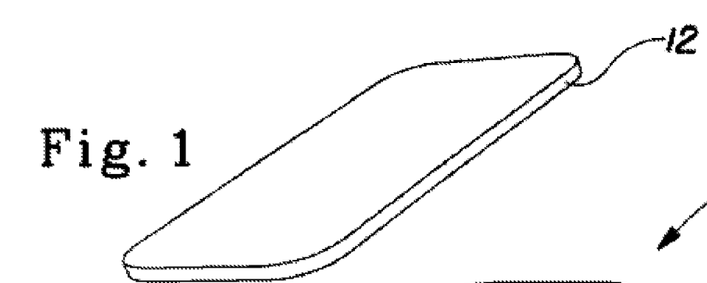
FIG. 1 is a perspective view of a strip of material.
Figure 2:
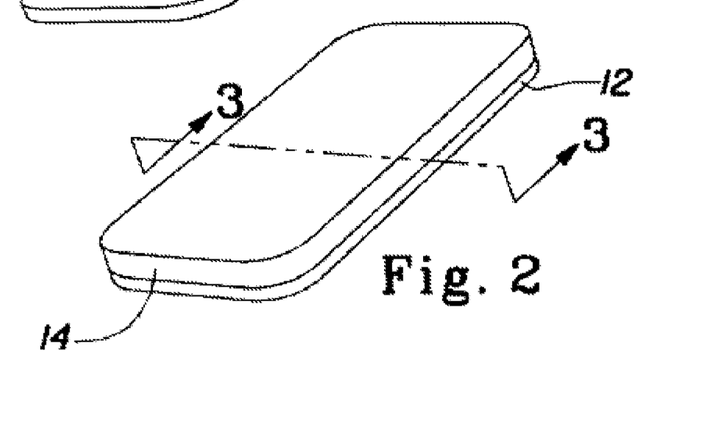
FIG. 2 is a perspective view of an embodiment of the present invention, comprising the flat strip of FIG. 1 coated with an oral care substance.
Figure 3:
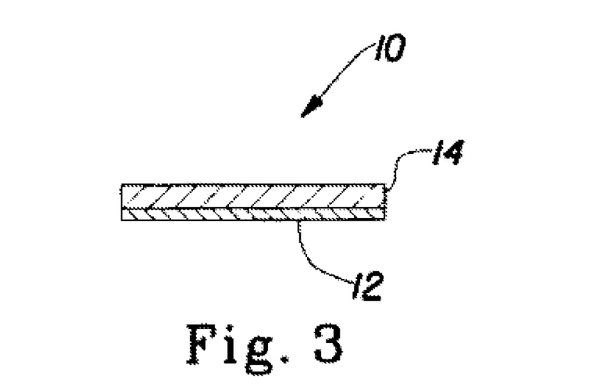
FIG. 3 is a cross-section view thereof, taken along section line 3-3 of FIG. 2, comprising the flat strip having a thickness less than that of the substance coated thereon.

As used herein, and shown in FIGS. 1 to 3, the term oral care strip 10 means a delivery system for an oral care substance which comprises a strip of material 12, which can be initially substantially flat. The strip of material 12 may be a single layer of polymer, woven, non-woven, foil, paper, rubber, or a combination thereof, such as a laminate. The strip of material may be a section of thin material having a length longer than the width with a thickness less than the width. An example is a length from about 2 to about 3 times the width. Alternatively, the length and width are about equivalent. In an example, the length is from about 1 to about 5 cm, alternatively from about 2 to about 5 cm. While the thickness may vary, an example strip of material may have a thickness between about 0.1 micrometer and about 1500 micrometer (µm).

Integral with, applied to or coated on to a strip of material 12 is an oral care substance 14, which in certain embodiments may be a homogeneous fluid, uniformly and continuously coated onto the strip of material. However, the oral care substance may alternatively be a laminate or separated layers of components, an amorphous mixture of components, separate stripes or spots or other patterns of different components, or a combination of these structures including a continuous coating of oral care substance 14 along a longitudinal axis of a portion of a strip of material 12. The oral care substance may contain or is itself an active, such as a composition, compound, or mixture capable of influencing or effecting a desired change in appearance and/or structure of the surface it contacts. Example actives include: oxalic acid, potassium salts of oxalic acid, hydrogen peroxide, carbamide peroxide, sodium fluoride, sodium monofluorophosphate, pyrophosphate, chlorhexidine, polyphosphate, triclosan, and enzymes. Examples of appearance and structural changes include, but are not necessarily limited to: desensitizing, whitening, stain bleaching, stain removal, remineralization to form fluorapatite, plaque removal, and tartar removal.

The term "dentifrice", as used herein, includes tooth or subgingival-paste, gel, powder, or liquid formulations unless otherwise specified. The dentifrice composition may be a single phase composition or may be a combination of two or more separate dentifrice compositions. The dentifrice composition may be in any desired form, such as deep striped, surface striped, multilayered, having a gel surrounding a paste, or any combination thereof. Each dentifrice composition in a dentifrice comprising two or more separate dentifrice compositions may be contained in a physically separated compartment of a dispenser and dispensed side-by-side.

As used herein "TREK-1" is a TWIK-1 related K channel found in mammals as reported for example by M. Fink et. al (Fink, M.; Duprat, F.; Lesage, F.; Reyes, R.; Romey, G.; Heurteaux, C.; Lazdunski, M. (1996). "Cloning, functional expression and brain localization of a novel unconventional outward rectifier K+ channel". *The EMBO Journal* 15 (24): 6854-6862).

The term "TREK-1 agonist" as used herein refers to a molecule or substance that gives rise to the activation of the TREK-1 receptor in a cell based TREK-1 assay, which is a fluorescence-based assay using a dye [Red (R8126) from Molecular Devices, Sunnyvale, Calif.] that is sensitive to changes in the membrane potential. Activation of TREK-1 leads to cell membrane depolarization as positive ions enter the cell. The fluorescent signal increases in intensity as the dye follows the positively charged ions inside the cell. The fluorescence measure is then captured via conventional detectors, such as a Fluorescent Imaging Plate Reader (FLIPR) device, for example FLIPR Tetra® High Throughput Cellular Screening System from Molecular Devices® Sunnyvale, Calif.

TREK-1 agonists of the present invention include: L-carvone; gamma-dodecalactone; 4-ethyloctanoic acid; 2-Isopropyl-5-methyl-2-hexenal; 4-Methylnonanoic acid; trans-2-Decenal; Tributyl Phosphate; Dioctyl Adipate; Bis(2-ethyl hexyl)Phosphate; Spearmint oil; Synthetic Cassia; Methyl salicylate; Wintergreen oil; Thymol; and Eugenol. In certain embodiments TREK-1 agonists may be present from about 0.01% to about 0.8% or from about 0.1 to about 0.5, by weight of the composition.

The term "TREK-1 antagonist" as used herein refers to any component which at a concentration of about 1 mM gives a reduction in calcium flux count of at least about 1000 counts below the activation of TREK-1 by about 100 mM of potassium chloride in the cell according to the FLIPR method as discussed herein. The term "count" is defined as the change in fluorescence of the transfected cell lines due to the influx of potassium across the cell membrane, which causes activation of voltage sensitive dye present within the cells. The antagonistic effect may also be measured at by looking at lower concentrations of the receptor agonist at 50 mM or lower.

Antagonists to TREK-1 may include one or more of the following: ((R)-1,4-Dihydro-2,6-dimethyl-4-(3-nitrophenyl)-3,5-pyridinedicarboxylic acid, 3-(4,4-diphenyl-1-piperidinyl)propyl methyl ester hydrochloride); or (2-[(2-Aminoethoxy)methyl]-4-(2-chlorophenyl)-1,4-dihydro-6-methyl-3,5-pyridinedicarboxylic acid 3-ethyl 5-methyl ester benzenesulfonate); or (1,4-Dihydro-2,6-dimethyl-4-(2-nitrophenyl)-3,5-pyridinedicarboxylic acid dimethyl ester); ((E)-1-[Bis(4-fluorophenyl)methyl]-4-(3-phenyl-2-propenyl)piperazine dihydrochloride); or (N-(2-Hydroxyethyl)-5Z,8Z,11Z,14Z-eicosatetraenamide); or (1-[4,4-Bis(4-fluorophenyl)butyl]-4-[4-chloro-3(trifluoromethyl)phenyl]-4-piperidinol); or ((1S,2S)-2-8 2[[3-(2-Benzimidazolyl)propyl]methylamino]ethyl]-6-fluoro-1,2,3,4-tetrahydro-1-isopropyl-2-naphthyl methoxyacetate dihydrochloride hydrate); or Spadin; or L-methionine; and/or methioninol.

The term "TREK-1 enhancer" as used herein refers to any component that boosts the potassium flux activity of a compound that directly activates TREK-1, but does not directly activate TREK-1.

It is highly desirable that consumer products for use in cleaning and care of the oral cavity impart a fresh and clean feeling, as this provides consumers with a signal of continuing freshness and cleanliness. In addition to the feeling of cleanliness, consumers also want to experience the benefits of oral care actives like anti-tartar agents, through their oral care regimen. The ability to formulate a consumer acceptable oral care composition, however, raises challenges; as many of the components used to impart a flavor, deliver a benefit, or that are part of the base for the oral care composition add unwanted tastes and/or sensations along with the targeted benefit for which they are added. Thus, formulating oral care compositions can be a balancing act between acceptable flavor and acceptable benefits.

In addition to the TREK-1 agonists the oral care compositions of the present invention may include one or more of the following components, such as metal salts, sweeteners, carrier materials, antimicrobial agents, bad breath reduction agents, bleaching agents separate from hydrogen peroxide, surfactants, flavors, anti-tartar agents, colorants, sensates, abrasive polishing materials, thickening materials, humectants, and other additives.

Active and other ingredients useful with the present invention may be categorized or described herein by their cosmetic and/or therapeutic benefit or their postulated mode of action or function. However, it is to be understood that the active and other ingredients useful herein can, in some instances, provide more than one cosmetic and/or therapeutic benefit or function or operate via more than one mode of action. Therefore, classifications herein are made for the sake of convenience and are not intended to limit an ingredient to the particularly stated function(s) or activities listed.

A metal salt includes zinc salts, stannous salts, potassium salts, copper salts, alkali metal bicarbonate slats, and combinations thereof. Metal salts have a wide range of functions from antimicrobial agents to sensitivity agents or buffers. The oral care compositions of the present invention may contain metal salt in an amount from about 0.05% to about 11%, from about 0.5% to about 7%, or from about 1% to about 5%, by total weight of the composition.

It is common to have a fluoride compound present in dentifrices and other oral care compositions in an amount sufficient to give a fluoride ion concentration in the composition of from about 0.0025% to about 5.0% or from about 0.005% to about 2.0%, by weight of the oral care composition to provide anticaries effectiveness. A wide variety of fluoride ion-yielding materials can be employed as sources of soluble fluoride in the present invention. Representative fluoride ion sources include: stannous fluoride, sodium fluoride, potassium fluoride, amine fluoride, sodium monofluorophosphate, indium fluoride, amine fluorides such as Olaflur, and many others. Examples of suitable fluoride ion-yielding materials are found in U.S. Pat. No. 3,535,421 and U.S. Pat. No. 3,678,154.

Stannous salts include stannous fluoride, stannous chloride, stannous iodide, stannous chlorofluoride, stannous acetate, stannous hexafluorozirconate, stannous sulfate, stannous lactate, stannous tartrate, stannous gluconate, stannous citrate, stannous malate, stannous glycinate, stannous pyrophosphate, stannous metaphosphate, stannous oxalate, stannous phosphate, stannous carbonate, and combinations thereof. Dentifrices containing stannous salts, particularly stannous fluoride and stannous chloride, are described in U.S. Pat. No. 5,004,597. Other descriptions of stannous salts are found in U.S. Pat. No. 5,578,293. and in U.S. Pat. No. 5,281,410. In addition to the stannous ion source, other ingredients used to stabilize the stannous may be included, such as the ingredients described in U.S. Pat. No. 5,004,597 and U.S. Pat. No. 5,578,293.

Zinc salts include zinc fluoride, zinc chloride, zinc iodide, zinc chlorofluoride, zinc actetate, zinc hexafluorozirconate, zinc sulfate, zinc lactate, zinc tartrate, zinc gluconate, zinc citrate, zinc malate, zinc glycinate, zinc pyrophosphate, zinc metaphosphate, zinc oxalate, zinc phosphate, zinc carbonate, and combinations thereof.

Potassium salts include potassium nitrate, potassium citrate, potassium oxalate, potassium bicarbonate, potassium acetate, potassium chloride, and combinations thereof.

In certain embodiments, the copper salt is selected from copper fluoride, copper chloride, copper iodide, copper chlorofluoride, copper actetate, copper hexafluorozirconate, copper sulfate, copper lactate, copper tartrate, copper gluconate, copper citrate, copper malate, copper glycinate, copper pyrophosphate, copper metaphosphate, copper oxalate, copper phosphate, copper carbonate, and combinations thereof. In a further embodiment, the copper salt is selected from copper gluconate, copper acetate, copper glycinate, and combinations thereof.

Alkali metal bicarbonate salts are soluble in water and unless stabilized, tend to release carbon dioxide in an aqueous system. Sodium bicarbonate, also known as baking soda, can be used as an alkali metal bicarbonate salt. The alkali metal bicarbonate salt also functions as a buffering agent. Because of the pH at which alkali metal bicarbonate salts buffer, the bicarbonate salt may be in a phase separate from the stannous ion source. In certain embodiments, the oral care compositions of the present invention may contain from about 0.5% to about 50%, from about 0.5% to about 30%, from about 2% to about 20%, or from about 5% to about 18% of an alkali metal bicarbonate salt, by weight of the oral care composition.

Some metal salts that may be used in the present invention, such as zinc chloride, zinc citrate, copper gluconate, and zinc gluconate, are also associated with an off taste described as dirty, dry, earthy, metallic, sour, bitter, and astringent. See, for example, an article by Hu, Hongzhen, et al in *Nature Chemical Biology* (2009), 5 (3), Pages 183-190, entitled: Zinc Activates Damage-Sensing TRPA1 Ion Channels.

Sweeteners include saccharin, chloro-sucrose (sucralose), steviolglycosides, rebaudioside A, rebaudioside B, rebaudioside C, rebaudioside D, rebaudioside E, rebaudioside F, dulcoside A, dulcoside B, rubusoside, stevia, stevioside, acesulfame K, xylitol, neohesperidine DC, alitame, aspartame, neotame, alitame, thaumatin, cyclamate, glycyrrhizin, mogroside IV, mogroside V, Luo Han Guo sweetener, siamenoside, monatin and its salts (monatin SS, RR, RS, SR), curculin, monellin, mabinlin, brazzein, hemandulcin, phyllodulcin, glycyphyllin, phloridzin, trilobatin, baiyanoside, osladin, polypodoside A, pterocaryoside A, pterocaryoside B, mukurozioside, phlomisoside I, periandrin I, abrusoside A, cyclocarioside I,N—[NT-[3-(3-hydroxy-4-methoxyphenyl)propyl]-L-α-aspartyl]-L-phenylalanine 1-methyl ester, N—[NT-[3-(3-hydroxy-4-methoxyphenyl)-3-methylbutyl]-L-α-aspartyl]-L-phenylalanine 1-methyl ester, N—[NT-[3-(3-methoxy-4-hydroxyphenyl)propyl]-L-α-aspartyl]-L-phenylalanine 1-methyl ester, salts thereof, and combinations thereof.

Rebiana is a steviolglycoside from Cargill Corp., Minneapolis, Minn., which is an extract from the leaves of the Stevia rebaudiana plant (hereinafter referred to as "Rebiana"). This is a crystalline diterpene glycoside, about 300× sweeter than sucrose. Examples of suitable stevioglycosides which may be combined include rebaudioside A, rebaudioside B, rebaudioside C, rebaudioside D, rebaudioside E, rebaudioside F, dulcoside A, dulcoside B, rubusoside, stevioside, or steviolbioside. According to particularly desirable embodiments of the present invention, the combination of high-potency sweeteners comprises rebaudioside A in combination with rebaudioside B, rebaudioside C, rebaudioside F, rebaudioside F, stevioside, steviolbioside, dulcoside A. Sweeteners are generally included in an oral care composition at a level of about 0.0005% to about 2%, by total weight of the oral care composition.

Carrier materials include water, glycerin, sorbitol, polyethylene glycols having a molecular weight of less than about 50,000, propylene glycol and other edible polyhydric alcohols, ethanol, or combinations thereof. The oral care compositions of the present invention may include from about 5% to about 80%, by weight of the composition, of a carrier material. In certain embodiments, the compositions of the present invention may contain carrier materials in an amount of from about 10% to about 40%, by total weight of the oral care composition.

Antimicrobial agents include quaternary ammonium compounds. Those useful in the present invention include, for example, those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl(2-phenoxyethyl) ammonium bromide, benzyl dimethoylstearyl ammonium chloride, quaternized 5-amino-1,3-bis(2-ethyl-hexyl)-5-methyl hexahydropyrimidine, benzalkonium chloride, benzethonium chloride and methyl benzethonium chloride are exemplary of typical quaternary ammonium antibacterial agents.

Other quaternary ammonium compounds include the pyridinium compounds. Examples of pyridinium quaternary ammonium compounds include bis[4-(R-amino)-1-pyridinium]alkanes as disclosed in U.S. Pat. No. 4,206,215, and cetylpyridinium and tetradecylpyridinium halide salts (i.e., chloride, bromide, fluoride and iodide).

The oral care compositions of the present invention may also include other antimicrobial agents including non-cationic antimicrobial agents such as halogenated diphenyl ethers, phenolic compounds including phenol and its homologs, mono and poly-alkyl and aromatic halophenols, resorcinol and its derivatives, xylitol, bisphenolic compounds and halogenated salicylanilides, benzoic esters, and halogenated carbanilides. Also useful antimicrobials are enzymes, including endoglycosidase, papain, dextranase, mutanase, and combinations thereof. Such agents are disclosed in U.S. Pat. No. 2,946,725 and in U.S. Pat. No. 4,051,234. Examples of other antimicrobial agents include chlorhexidine, and flavor oils such as thymol. The compositions of the present invention may contain antimicrobial agents in an amount of from about 0.035% or more, from about 0.1% to about 1.5%, from about 0.045% to about 1.0%, or from about 0.05% to about 0.10%, by total weight of the oral care composition.

Bleaching agents include peroxides, perborates, percarbonates, peroxyacids, persulfates, and combinations thereof. Suitable peroxide compounds include hydrogen peroxide, urea peroxide, calcium peroxide, sodium peroxide, zinc peroxide, or combinations thereof. One example of a percarbonate is sodium percarbonate. An example of a persulfate includes oxones. Some bleaching agents provide a cool burn sensation within an oral care composition, for example peroxides and percarbonates. The compositions of the present invention may contain bleaching agents in an amount of from about 0.01% to about 30%, from about 0.1% to about 10%, or from about 0.5% to about 5%, by total weight of the oral care composition.

Surfactants may include anionic surfactants such as organophosphate, which include alkyl phosphates. These surface active organophosphate agents have a strong affinity for enamel surfaces and have sufficient surface binding propensity to desorb pellicle proteins and remain affixed to enamel surfaces. Suitable examples of organophosphate compounds include mono-, di- or triesters represented by the general structure below wherein Z1, Z2, or Z3 may be identical or different, at least one being an organic moiety, in one embodiment selected from linear or branched, alkyl or alkenyl group of from 1 to 22 carbon atoms, optionally substituted by one or more phosphate groups; alkoxylated alkyl or alkenyl, (poly)saccharide, polyol or polyether group.

Some other organophosphate agents include alkyl or alkenyl phosphate esters represented by the following structure:

wherein R1 represents a linear or branched, alkyl or alkenyl group of from 6 to 22 carbon atoms, optionally substituted by one or more phosphate groups; n and m, are individually and separately, 2 to 4, and a and b, individually and separately, are 0 to 20; Z2 and Z3 may be identical or different, each represents hydrogen, alkali metal, ammonium, protonated alkyl amine or protonated functional alkyl amine such as an alkanolamine, or a R1-(OCnH2n)a(OCmH2m)b-group. Examples of suitable agents include alkyl and alkyl(poly)alkoxy phosphates such as lauryl phosphate; PPG5 ceteareth-10 phosphate; Laureth-1 phosphate; Laureth-3 phosphate; Laureth-9 phosphate; Trilaureth-4 phosphate; C12-18 PEG 9 phosphate; Sodium dilaureth-10 phosphate. In one embodiment, the alkyl phosphate is polymeric. Examples of polymeric alkyl phosphates include those containing repeating alkoxy groups as the polymeric portion, in particular 3 or more ethoxy, propoxy isopropoxy or butoxy groups.

Zwitterionic or amphoteric surfactants useful in the present invention include derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, such as carboxy, sulfonate, sulfate, phosphate or phosphonate. Suitable amphoteric surfactants include betaine surfactants such as disclosed in U.S. Pat. No. 5,180,577 to Polefka et al. Typical alkyl dimethyl betaines include decyl betaine or 2-(N-decyl-N,N-dimethylammonio)acetate, coco betaine or 2-(N-coco-N, N-dimethyl ammonio)acetate, myristyl betaine, palmityl betaine, lauryl betaine, cetyl betaine, stearyl betaine, etc. Amphoteric surfactants useful herein further include amine oxide surfactants. The amidobetaines are exemplified by cocoamidoethyl betaine, cocamidopropyl betaine (CAPB), and lauramidopropyl betaine. The unwanted tastes often associated with these surfactants are soapy, bitter, chemical, or artificial.

Additional suitable polymeric organophosphate agents include dextran phosphate, polyglucoside phosphate, alkyl polyglucoside phosphate, polyglyceryl phosphate, alkyl polyglyceryl phosphate, polyether phosphates and alkoxylated polyol phosphates. Some specific examples are PEG phosphate, PPG phosphate, alkyl PPG phosphate, PEG/PPG phosphate, alkyl PEG/PPG phosphate, PEG/PPG/PEG phosphate, dipropylene glycol phosphate, PEG glyceryl phosphate, PBG (polybutylene glycol)phosphate, PEG cyclodextrin phosphate, PEG sorbitan phosphate, PEG alkyl sorbitan phosphate, and PEG methyl glucoside phosphate. Suitable non-polymeric phosphates include alkyl mono glyceride phosphate, alkyl sorbitan phosphate, alkyl methyl glucoside phosphate, alkyl sucrose phosphates. The impurities in these phosphates may induce a burning sensation. Impurities may include dodecanol, dodecanal, benzaldehyde, and other TRPA1 or TRPV1 agonists.

Cationic surfactants useful in the present invention include derivatives of quaternary ammonium compounds having one long alkyl chain containing from about 8 to 18 carbon atoms such as lauryl trimethylammonium chloride, cetyl trimethylammonium bromide, coconut alkyltrimethylammonium nitrite, cetyl pyridinium fluoride, etc. Quaternary ammonium halides having detergent properties can be used, such as those described in U.S. Pat. No. 3,535,421. Certain cationic surfactants can also act as germicides in the oral care compositions disclosed herein.

Examples of some flavors and flavor components that may be used in oral care compositions are mint oils, wintergreen, clove bud oil, cassia, sage, parsley oil, marjoram, lemon, orange, propenyl guaethol, heliotropine, 4-cis-heptenal, diacetyl, methyl-p-tert-butyl phenyl acetate, methyl salicylate, ethyl salicylate, 1-menthyl acetate, oxanone, α-irisone, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, octanol, octanal, decanol, decanal, phenylethyl alcohol, benzyl alcohol, α-terpineol, linalool, limonene, citral, neral, geranial, geraniol nerol, maltol, ethyl maltol, anethole, dihydroanethole, carvone, menthone, β-damascenone, ionone, γ-decalactone, γ-nonalactone, γ-undecalactone, or combinations thereof. Generally suitable flavoring ingredients are chemicals with structural features and functional groups that are less prone to redox reactions. These include derivatives of flavor chemicals that are saturated or contain stable aromatic rings or ester groups.

Flavors are generally present in an amount of from about 0.4% to about 5% or from about 1% to about 3%, by total weight of the oral care composition.

Anti-tartar agents include pyrophosphate salts as a source of pyrophosphate ion. The pyrophosphate salts useful in the present compositions include, for example, the mono-, di- and tetraalkali metal pyrophosphate salts and combinations thereof. Disodium dihydrogen pyrophosphate (Na2H2P2O7), sodium acid pyrophosphate, tetrasodium pyrophosphate (Na4P2O7), and tetrapotassium pyrophosphate (K4P207) in their unhydrated as well as hydrated forms are further species. In compositions of the present invention, the pyrophosphate salt may be present in one of three ways: predominately dissolved, predominately undissolved, or a combination of dissolved and undissolved pyrophosphate. The amount of pyrophosphate salt useful in making these compositions is any tartar control effective amount. In varying embodiments, the amount of pyrophosphate salt may be from about 1.5% to about 15%, from about 2% to about 10%, or about 3% to about 8%, by total weight of the oral care composition.

Examples of some colorants that may be used in oral care compositions include D&C Yellow No. 10, FD&C Blue No. 1, FD&C Red No. 40, D&C Red No. 33 and combinations thereof. In certain embodiments, the composition comprises colorant in an amount of from about 0.0001% to about 0.1% or from about 0.001% to about 0.01%, by weight of the oral care composition. Some colorants provide an unwanted taste, for example, D&C Red No. 33. The unwanted tastes often associated with this colorant are metallic, sharp, or chemical. Colorants are generally present in an amount of from about 0.001% to about 0.5%, by weight of the oral care composition.

Sensates may also be part of an oral care composition. Sensate molecules such as cooling, warming, and tingling agents are useful to deliver signals to the user. Sensates are generally present in an amount of from about 0.001% to about 0.8%, by weight of the oral care composition. The most well-known cooling sensate compound is menthol, particularly L-menthol, which is found naturally in peppermint oil notably of *Mentha arvensis* L and *Mentha viridis* L. Of the menthol isomers the L-isomer occurs most widely in nature and is typically what is referred by the name menthol having coolant properties. L-menthol has the characteristic peppermint odor, has a clean fresh taste and exerts a cooling sensation when applied to the skin and mucosal surfaces. Other isomers of menthol (neomenthol, isomenthol and neoisomenthol) have somewhat similar, but not identical odor and taste, for instance having disagreeable odor and taste described as earthy, camphor, musty, etc. The biggest difference among the isomers is in their cooling potency. L-menthol provides the most potent cooling, by having the lowest cooling threshold of about 800 ppb, which is the concentration level where the cooling effect can be clearly recognized. At this level, there is no cooling effect for the other isomers. For example, d-neomenthol is reported to have a cooling threshold of about 25,000 ppb and 1-neomenthol about 3,000 ppb. [R. Emberger and R. Hopp, "Synthesis and Sensory Characterization of Menthol Enantiomers and Their Derivatives for the Use in Nature Identical Peppermint Oils," Specialty Chemicals (1987), 7(3), 193-201].

Among synthetic coolants, many are derivatives of—or are structurally related to menthol, for example containing the cyclohexane moiety, and derivatized with functional groups including carboxamide, ketal, ester, ether and alcohol. Examples include the ρ-menthanecarboxamide compounds such as N-ethyl-ρ-menthan-3-carboxamide, known commercially as "WS-3", and others in the series, such as WS-5 (N-ethoxycarbonylmethyl-ρ-menthan-3-carboxamide), WS-12 (1R*,2S*)—N-(4-Methoxyphenyl)-5-methyl-2-(1-methylethyl)cyclohexanecarboxamide] and WS-14 (N-tert-butyl-ρ-menthan-3-carboxamide). Examples of menthane carboxy esters include WS-4 and WS-30. An example of a synthetic carboxamide coolant that is structurally unrelated to menthol is N,2,3-trimethyl-2-isopropylbutanamide, known as "WS-23". Additional examples of synthetic coolants include alcohol derivatives such as 3-(1-menthoxy)-propane-1,2-diol known as TK-10, isopulegol (under the tradename Coolact P) and ρ-menthane-3,8-diol (under the tradename Coolact 38D) all available from Takasago Corp., Tokyo, Japan; menthone glycerol acetal known as MGA; menthyl esters such as menthyl acetate, menthyl acetoacetate, menthyl lactate known as Frescolat® supplied by Symrise AG, Holzminden, Germany, and monomenthyl succinate under the tradename Physcool from V. Mane FILS, Notre Dame, France. TK-10 is described in U.S. Pat. No. 4,459,425. Other alcohol and ether derivatives of menthol are described in GB 1,315,626 and in U.S. Pat. Nos. 4,029,759; 5,608,119; and 6,956,139. WS-3 and other carboxamide cooling agents are described in U.S. Pat. Nos. 4,136,163; 4,150,052; 4,153,679; 4,157,384; 4,178,459 and 4,230,688.

Additional N-substituted ρ-menthane carboxamides are described in WO 2005/049553A1 including N-(4-cyanomethylphenyl)-ρ-menthanecarboxamide, N-(4-sulfamoylphenyl)-ρ-menthanecarboxamide, N-(4-cyanophenyl)p-menthanecarboxamide, N-(4-acetylphenyl)-ρ-menthanecarboxamide, N-(4-hydroxymethylphenyl)-ρ-menthanecarboxamide and N-(3-hydroxy-4-methoxyphenyl)-ρ-menthanecarboxamide. Other N-substituted ρ-menthane carboxamides include amino acid derivatives such as those disclosed in WO 2006/103401 and in U.S. Pat. Nos. 4,136,163; 4,178,459; and 7,189,760 such as N-((5-methyl-2-(1-methylethyl)cyclohexyl)carbonyl)glycine ethyl ester and N-((5-methyl-2-(1-methylethyl)cyclohexyl)carbonyl)alanine ethyl ester. Menthyl esters including those of amino acids such as glycine and alanine are disclosed e.g., in EP 310,299 and in U.S. Pat. Nos. 3,111,127; 3,917,613; 3,991,178; 5,703,123; 5,725,865; 5,843,466; 6,365,215; 6,451,844; and 6,884,903. Ketal derivatives are described, e.g., in U.S. Pat. Nos. 5,266,592; 5,977,166; and 5,451,404. Additional agents that are structurally unrelated to menthol but have been reported to have a similar physiological cooling effect include alpha-keto enamine derivatives described in U.S. Pat. No. 6,592,884 including 3-methyl-2-(1-pyrrolidinyl)-2-cyclopenten-1-one (3-MPC), 5-methyl-2-(1-pyrrolidinyl)-2-cyclopenten-1-one (5-MPC), and 2,5-dimethyl-4-(1-pyrrolidinyl)-3(2H)-furanone (DMPF); icilin (also known as AG-3-5, chemical name 1-[2-hydroxyphenyl]-4-[2-nitrophenyl]-1,2,3,6-tetrahydropyrimidine-2-one) described in Wei et al., J. Pharm. Pharmacol. (1983), 35:110-112. Reviews on the coolant activity of menthol and synthetic coolants include H. R. Watson, et al. J. Soc. Cosmet. Chem. (1978), 29, 185-200 and R. Eccles, J. Pharm. Pharmacol., (1994), 46, 618-630.

Additional agents that are structurally unrelated to menthol but have been reported to have a similar physiological cooling effect include alpha-keto enamine derivatives described in U.S. Pat. No. 6,592,884 including 3-methyl-2-(1-pyrrolidinyl)-2-cyclopenten-1-one (3-MPC), 5-methyl-2-(1-pyrrolidinyl)-2-cyclopenten-1-one (5-MPC), and 2,5-dimethyl-4-(1-pyrrolidinyl)-3(2H)-furanone (DMPF); icilin (also known as AG-3-5, chemical name 1-[2-hydroxyphenyl]-4-[2-nitrophenyl]-1,2,3,6-tetrahydropyrimidine-2-one) described in Wei et al., J. Pharm. Pharmacol. (1983), 35:110-112 and phosphine oxides as reported in U.S. Pat. No. 4,070,496.

Some examples of warming sensates include ethanol; capsicum; nicotinate esters, such as benzyl nicotinate; polyhydric alcohols; capsicum powder; a capsicum tincture; capsicum extract; capsaicin; homocapsaicin; homodihydrocapsaicin; nonanoyl vanillyl amide; nonanoic acid vanillyl ether; vanillyl alcohol alkyl ether derivatives such as vanillyl ethyl ether, vanillyl butyl ether, vanillyl pentyl ether, and vanillyl hexyl ether; isovanillyl alcohol alkyl ethers; ethylvanillyl alcohol alkyl ethers; veratryl alcohol derivatives; substituted benzyl alcohol derivatives; substituted benzyl alcohol alkyl ethers; vanillin propylene glycol acetal; ethylvanillin propylene glycol acetal; ginger extract; ginger oil; gingerol; zingerone; or combinations thereof. Warming sensates are generally included in an oral care composition at a level of about 0.05% to about 2%, by weight of the oral care composition.

Abrasive polishing material can be any material that does not excessively abrade dentin. The oral care compositions of the present invention may comprise abrasive polishing material in an amount of from about 6% to about 70% or from about 10% to about 50%, by weight of the oral care composition. Typical abrasive polishing materials include silicas including gels and precipitates; aluminas; phosphates including orthophosphates, polymetaphosphates, and pyrophosphates; and mixtures thereof. Specific examples include dicalcium orthophosphate dihydrate, calcium pyrophosphate, tricalcium phosphate, calcium polymetaphosphate, insoluble sodium polymetaphosphate, rice hull silica, hydrated alumina, beta calcium pyrophosphate, calcium carbonate, and resinous abrasive materials such as particulate condensation products of urea and formaldehyde, and others, such as disclosed in U.S. Pat. No. 3,070,510. In certain embodiments, if the oral composition or particular phase comprises a polyphosphate having an average chain length of about 4 or more, calcium containing abrasives and alumina are not preferred abrasives.

Silica dental abrasives of various types are often used in oral care compositions due to their exceptional dental cleaning and polishing performance without unduly abrading tooth enamel or dentine. Silica abrasive polishing materials that may be used in the present invention, as well as other abrasives, generally have an average particle size ranging between about 0.1 µm to about 30 µm or from about 5 µm to about 15 µm. The abrasive can be precipitated silica or silica gels, such as the silica xerogels described in U.S. Pat. No. 3,538,230 and U.S. Pat. No. 3,862,307. Silica xerogels marketed under the trade name "Syloid" by the W.R. Grace & Company, Davison Chemical Division, Augusta, Ga. may be used. Also precipitated silica materials, such as those marketed by the J. M. Huber Corporation, Edison, N.J. under the trade name, "Zeodent", particularly the silica carrying the designation "Zeodent 119", may be used. The types of silica dental abrasives useful in the oral care compositions of the present invention are described in more detail in U.S. Pat. No. 4,340,583; and U.S. Pat. Nos. 5,589,160; 5,603,920; 5,651,958; 5,658,553; and 5,716,601.

Thickening material or binders may be used to provide a desirable consistency to the oral care compositions of the present invention. For example, when the oral care compositions are in the form of dentifrices, topical oral gels, mouthrinse, denture product, mouthsprays, lozenges, oral tablets, or chewing gums, the amount and type of the thickening material will depend upon the form of the product. Thickening materials include carboxyvinyl polymers, carrageenan, hydroxyethyl cellulose, and water soluble salts of cellulose ethers such as sodium carboxymethylcellulose and sodium hydroxyethyl cellulose. Natural gums such as gum karaya, xanthan gum, gum arabic, and gum tragacanth can also be used. Colloidal magnesium aluminum silicate or finely divided silica can be used as part of the thickening material to further improve texture. Thickening materials can be used in an amount from about 0.1% to about 15%, by weight of the oral care composition.

Humectants keep oral care compositions from hardening upon exposure to air and certain humectants can also impart desirable sweetness of flavor to dentifrice compositions. Suitable humectants for use in the present invention include glycerin, sorbitol, polyethylene glycol, propylene glycol, xylitol, and other edible polyhydric alcohols. The oral care compositions of the present invention may comprise humectants in an amount of from about 0% to about 70% or from about 15% to about 55%, by weight of the oral care composition.

EXAMPLES

The following Examples serve to illustrate the invention without limiting it.

Cell Culture

HEK-293 cells used in the assay are stably transfected with a truncated version of mouse TREK-1 nucleotide sequence (mTREK-1t) by Capital Biosciences (Rockville, Md.). The actual sequence used is shown in SEQ ID NO: 1, and is based on a mouse TREK-1 sequence that was published on 2 Oct. 1996 (Fink et al., The EMBO Journal vol. 15 no. 24 pp. 6854-6862, 1996). HEK-293 cells transfected with mTREK-1t (mTREK-1t cells) are grown in 18 ml growth medium comprising high glucose DMEM (Dulbecco's Modification of Eagle's Medium), supplemented with 10% FBS (fetal bovine serum), 100 µg/ml Penicillin/streptomycin, and 100 µg/ml G418 in a 75 cm$^2$ flask for 2-3 days in a mammalian cell culture incubator set at 37° C., 5% $CO_2$ and 90% humidity. In certain embodiments a TREK-1 sequence may be used that has at least about 70% sequence identity with the mTREK-1t DNA sequence.

FLIPR Membrane Potential Assay

To detach the mTREK-1t cells, the cells were washed once with 10 ml PBS (phosphate buffered saline), and then detached by adding 2 ml of 0.05% trypsin-EDTA solution in a 75 cm$^2$ flask for 1-2 min, followed by adding 10 ml of the growth medium to inactivate trypsin.

The cells were suspended in the growth medium at 800,000 cells/ml and 50 µl aliquots of the diluted cells loaded in each well of a 96-well plate.

The cell plates were placed in the mammalian cell culture incubator for sixteen hours, which was set at 37° C., 5% $CO_2$ and 90% humidity.

To each well, 50 µl of the membrane potential indicator dye (R8126 from Molecular Devices—Sunnyvale, Calif.) was added.

After 15-30 min incubation at room temperature and in the dark, the cell plates were transferred to a FLIPR-Tetra instrument (Molecular Devices, Sunnyvale, Calif.).

Following recordation of the baseline fluorescence, 20 µl of the compounds to be tested for activator potential (typically having a concentration range of 100 µM to 1 mM) were added to the wells of the cell plates containing the mTREK-1t cells, and the fluorescence change recorded using a FLIPR Tetra® High Throughput Cellular Screening System from Molecular Devices, Sunnyvale, Calif.

Tocrisolve™ Arachidonic acid (1 mM) was used as a positive control for activation of mTREK-1t.

The assay buffer was used as negative control.

The fluorescence signal was automatically recorded every 2 seconds for 3.5 minutes. The FLIPR emission filter used in the assay had a 540-590 nM band pass with excitation at 490 nm. The results were expressed as a percentage of the positive control fluorescence signal (activation).

Example 1

To determine the most effective TREK-1 agonists 246 Generally Recognized as Safe (GRAS) compounds were screened, using the FLIPR membrane potential assay, by the percent activity relative to potassium nitrate, as potassium nitrate is a commonly used active for reducing tooth sensitivity, and molecules that behave like it does on TREK-1, would be good candidates for reducing tooth sensitivity. TREK-1 channel agonists are shown below in TABLE 1.

activity than of the TREK-1 agonist potassium nitrate: 1,2-Dimethoxy 4-propenyl benzene; gamma-Dodecalactone; 4-Methyl-2-phenyl-2 Pentenal; 4-Ethyloctanoic Acid; 2-Isopropyl-5-methyl-2-hexenal; 4-Methylnonanoic acid; trans-2-Decenal; and 2-Phenylphenol. An activity of 50% or greater was used as typically anything at least half as good as a standard agonist is considered a good candidate, especially when the concentration used is significantly lower than that of standard agonist. Here 400 uM for agonists discovered, compared against 50 mM potassium nitrate.

Example 2

TABLE 2 below depicts molecules commonly used as plasticizers in the production of containers and not readily used as flavor components, but showed TREK-1 activity. The Activity Level shown in TABLE 2 represents the percentage of activity relative to 100% with 50 mM potassium nitrate, which was measured using the FLIPR membrane potential assay. Therefore, it was surprising to find that three of them provide TREK-1 activity with at least 50% of potassium nitrate level: tributyl phosphate; dioctyl adipate, and bis(2-ethyl hexyl)phosphate.

TABLE 2

| | Samples/Activity Level | | | | | | | |
|---|---|---|---|---|---|---|---|---|
| Sample Conc. | 50 mM Potassium Nitrate | Triethyl Citrate | Diisopropyl Adipate | Tributyl Phosphate | Acetyl Tributyl Citrate | Dipropyl Adipate | Dioctyl Adipate | Bis (2-ethyl hexyl) Phosphate |
| 0.505% | 100 | | | | | | | |
| 0.0330% | | 17.22 | 30.39 | 69 | 23.97 | 12.16 | 132.32 | 109.75 |
| 0.0167% | | 13.42 | 14.84 | 30.74 | 14.09 | 2.66 | 77.39 | 84.83 |
| 0.0083% | | 6.17 | 6.59 | 13.52 | 5.89 | 0.51 | 38.92 | 43.09 |
| 0.0042% | | 3.67 | 3.56 | 9.41 | 2.5 | 0 | 22.95 | 26.65 |
| 0.0021% | | 2.98 | 3.43 | 9.28 | 3.06 | 0 | 18.05 | 20.49 |
| 0.0010% | | 1.7 | 1.38 | 8.75 | 0.48 | 0 | 13.66 | 13.39 |
| 0.0005% | | 4.06 | 1.31 | 8.34 | 2.69 | 0 | 8.93 | 5.92 |

TABLE 1

| | Fluorescence per Sample concentration | | | | |
|---|---|---|---|---|---|
| Samples | 50 mM | 400 μM | 200 μM | 100 μM | 50 μM |
| 1,2-Dimethoxy 4-propenyl benzene | | 73.3 | 29.06 | 10.47 | 5.19 |
| gamma-Dodecalactone | | 65.83 | 18.74 | 3.41 | 1.77 |
| gamma-Tetradecalactone | | 15.89 | 9.82 | 3.54 | 3.21 |
| 4-Methyl-2-phenyl-2 Pentenal | | 70.07 | 52.14 | 27.14 | 16.52 |
| 4-Ethyloctanoic Acid | | 108.58 | 77.26 | 44.56 | 31 |
| 2-Isopropyl-5-methyl-2-hexenal | | 68.37 | 46.26 | 21.15 | 11.08 |
| 4-Methylnonanoic acid | | 89.95 | 79.94 | 38.53 | 24.78 |
| trans-2-Decenal | | 94.02 | 33.31 | 10.6 | 8.41 |
| 2-Phenylphenol | | 49.77 | 12.89 | 0.85 | 0.35 |
| Potassium Nitrate | 100 | | | | |

The data in TABLE 1 showed that the following molecules tested at 400 μM provided around 50% or greater As shown in TABLE 2, dioctyl adipate and bis (2-ethyl-hexyl)phosphate at 0.0167% showed greater than 70% comparable activity to that of potassium nitrate. At 0.033% Sample concentration, both these molecules had higher activity on TREK-1 than potassium nitrate and typically anything at least half as good as a standard agonist is considered a good candidate, especially when the concentration used is significantly lower than that of standard agonist. In this case 50 mM (0.505%) potassium nitrate versus 0.0167% and 0.033% for the agonists.

Example 3

TABLE 3 below shows the percentage of TREK-1 activity of spearmint and wintergreen oils and components of each, relative to potassium nitrate, which was determined using the FLIPR membrane potential assay.

TABLE 3

| | Sample Concentration | | | | | | | |
|---|---|---|---|---|---|---|---|---|
| Samples | 50 mM | 0.0333% | 0.0167% | 0.0083% | 0.0042% | 0.0021% | 0.0010% | 0.0005% |
| Potassium Nitrate | 100 | | | | | | | |
| Clove Bud oil | | 38.82 | 9.6 | 0 | 0 | 0 | 0 | 0 |
| Eugenol | | 45.6 | 8.61 | 0.53 | 0 | 0 | 0 | 0 |

TABLE 3-continued

| | Sample Concentration | | | | | | | |
|---|---|---|---|---|---|---|---|---|
| Samples | 50 mM | 0.0333% | 0.0167% | 0.0083% | 0.0042% | 0.0021% | 0.0010% | 0.0005% |
| L-Carvone | | 98.65 | 24.1 | 9.51 | 2.03 | 2.7 | 0.97 | 1.85 |
| Spearmint Native Oil | | 78.7 | 29.04 | 10.56 | 4.51 | 2.92 | 1.91 | 2.82 |
| Synthetic Cassia | | 56.25 | 21 | 10.32 | 5.24 | 4.46 | 1.67 | 2.25 |
| Methyl Salicylate | | 29.43 | 17.4 | 8.31 | 4.94 | 2.66 | 2.33 | 2.35 |
| Chinese Wintergreen Oil | | 34.65 | 17.51 | 9.08 | 3.91 | 3.19 | 2.98 | 3.16 |
| Thymol | | 65.22 | 31.4 | 6.73 | 4.09 | 3.86 | 4.82 | 4.57 |
| L- Menthol | | 29.12 | 10.29 | 4.21 | 2.08 | 2.14 | 2.5 | 2.81 |

The results in TABLE 3 show that Spearmint and Wintergreen oils have a higher activity than L-Menthol alone, and the oils contain ingredients that may be positive modulators of L-menthol and/or have TREK-1 activity on their own.

Example 4

For EXAMPLE 4 (TABLE 4) a panel of fourteen panelists evaluated the sensory profile experienced after brushing with a dentifrice containing high levels of menthol for two minutes, followed by rinsing with 15 ml of tap water for typically 5-20 seconds. Panelists brushed teeth with 1.5 grams of a test dentifrice (containing high menthol levels; Samples 4B-4I) or control (no menthol; Sample 4A) for 36 seconds and then expectorated. The dentifrice formulations (control and high L-Menthol) are shown below in TABLE 4. The dentifrices were made using conventional methods, such as the methods described in U.S. Pat. No. 5,939,052 and are shown below with amounts in weight % of total composition.

TABLE 5 below shows perceived cool burn sensation from varying levels of menthol in a spearmint flavor containing L-Carvone. Fourteen panelists separately brushed their teeth for two minutes with each of the toothpastes (4A-4I) and rated them separately according to a perceived cool burn sensation. After expectoration, the panelists rinsed their mouth with 15 ml of tap water, as they would during normal brushing, typically 5-20 seconds at room temperature (average temperature of 68° F.). The fourteen panelists began rating the cool burn sensation measurement in-mouth during brushing and after expectoration and water rinse over the course of 20 minutes. They assessed the cool burn sensation in their mouth and on their lips at 0 minutes after rinse, 5 minutes, 10 minutes, 15 minutes, and 20 minutes after rinse. Each panelist assigned a cool burn sensation of 0 (no sensation) to 60 (highest intensity sensation). At each evaluation, panelists were instructed to breathe in through pursed lips and evaluate overall sensation, for at least one full breath. In this test, a numerical score of 7.5 (this number was determined to be significant in terms of correlating to panelist response. A rating of 7.5 or higher means that the panelist will have some noticeability of the attribute, for

TABLE 4

| | Samples | | | | | | | | |
|---|---|---|---|---|---|---|---|---|---|
| Components | 4A | 4B | 4C | 4D | 4E | 4F | 4G | 4H | 4I |
| | Component Amounts per Sample | | | | | | | | |
| FD&C Blue #1 Color Solution | 0.045% | 0.045% | 0.045% | 0.045% | 0.045% | 0.045% | 0.045% | 0.045% | 0.045% |
| Sodium Fluoride | 0.243% | 0.243% | 0.243% | 0.243% | 0.243% | 0.243% | 0.243% | 0.243% | 0.243% |
| CARBOMER 956 | 0.300% | 0.300% | 0.300% | 0.300% | 0.300% | 0.300% | 0.300% | 0.300% | 0.300% |
| Sodium Saccharin | 0.300% | 0.300% | 0.300% | 0.300% | 0.300% | 0.300% | 0.300% | 0.300% | 0.300% |
| Sodium Phosphate, Monobasic, Monohydrate | 0.419% | 0.419% | 0.419% | 0.419% | 0.419% | 0.419% | 0.419% | 0.419% | 0.419% |
| Titanium Dioxide | 0.525% | 0.525% | 0.525% | 0.525% | 0.525% | 0.525% | 0.525% | 0.525% | 0.525% |
| Carboxymethy-cellulose Sodium | 0.800% | 0.800% | 0.800% | 0.800% | 0.800% | 0.800% | 0.800% | 0.800% | 0.800% |
| Spearmint Flavor | 1.000% | 1.000% | 1.000% | 1.000% | 1.000% | 1.000% | 1.000% | 1.000% | 1.000% |
| Added Menthol | 0% | 0.25% | 0.5% | 0.75% | 1.0% | 1.25% | 1.5% | 1.75% | 2.0% |
| Tribasic Sodium Phosphate Dodecahydrate | 1.100% | 1.100% | 1.100% | 1.100% | 1.100% | 1.100% | 1.100% | 1.100% | 1.100% |
| Sodium Lauryl Sulfate 28% Solution | 4.000% | 4.000% | 4.000% | 4.000% | 4.000% | 4.000% | 4.000% | 4.000% | 4.000% |
| Silica, Dental Type, NF (Zeodent 119) | 15.000% | 15.000% | 15.000% | 15.000% | 15.000% | 15.000% | 15.000% | 15.000% | 15.000% |
| SORBITOL SOLUTION LRS USP | 54.673% | 54.673% | 54.673% | 54.673% | 54.673% | 54.673% | 54.673% | 54.673% | 54.673% |
| Water Purified, USP, PhEur, JP, JSCI | QS* | QS* | QS* | QS* | QS* | QS* | QS* | QS* | QS* |

*QS refers to the term quantum sufficit, meaning as much as suffices, where the remainder of the formula hole is filled with this substance.

example a bitter taste or cool feeling), indicates a significant consumer noticeable sensation. Differences less than 7.5, but greater than 5.0 indicate the trending of the data on a specific attribute.

TABLE 5

| Evaluation | Samples | | | | | | | |
|---|---|---|---|---|---|---|---|---|
| Time Points | 4A | 4B | 4C | 4D | 4E | 4F | 4G | 4H | 4I |
| | Perceived Cool burn Sensation | | | | | | | |
| In-mouth | 31.1 | 33.0 | 37.1 | 36.9 | 40.9 | 40.0 | 42.5 | 40.4 | 44.4 |
| 0 min afte rinse | 33.3 | 33.6 | 38.0 | 38.2 | 41.9 | 40.5 | 44.1 | 42.3 | 46.1 |
| 5 min after rinse | 21.3 | 22.1 | 31.0 | 28.3 | 32.0 | 31.8 | 35.1 | 35.1 | 38.1 |
| 10 min after rinse | 7.4 | 13.3 | 21.0 | 12.8 | 21.6 | 20.4 | 25.9 | 26.9 | 29.9 |
| 15 min after rinse | 2.8 | 6.0 | 10.0 | 6.3 | 14.5 | 10.9 | 12.1 | 14.7 | 19.5 |
| 20 min after rinse | 1.8 | 2.9 | 7.1 | 3.3 | 5.8 | 4.5 | 7.2 | 7.5 | 8.8 |

As shown in TABLE 5, the cool burn sensation increases significantly for dentifrices which contain >0.25% added menthol (Samples 4B-4I). The cool burn sensation was significantly higher for the 0.5% added menthol and higher formulations (Samples 4C-4I) for spearmint flavor when compared to the control formulation (Sample 4A) which contained the spearmint flavor without the additional menthol. The cool burn sensation for the spearmint formulations, as shown in table 5, products 4B through 4I, was significantly high for 10-20 minutes after the water rinse.

The cool burn sensation was theorized as being driven by TRPA1 activation. The literature shows that neurons expressing TRPA1 may also express TRPM8 and TREK-1 (Zapia, et al., Pain. 2014 Jun. 3. pii: S0304-3959(14)00263-2). TREK-1 has also been shown to play a role in the modulation of heat pain associated with TRPV1, as it co-localized with TRPV1 (Alloui et al., EMBO J. Jun. 7, 2006; 25(11): 2368-2376). It is believed that the intense pain associated with TRPA1 and TRPM8 activation, caused by too much cold too quickly is modulated by the TREK-1 receptor, for example by events like getting a headache from eating ice cream too fast. The data in TABLE 5 shows that the quick onset of a cool burn sensation, as shown in Samples 4B through 4I is equal to the control flavor (Sample 4A) during the first 5 minutes after application, even out to 2.0% additional menthol. It is theorized that the L-Carvone in the spearmint activates TREK-1 to modulate the pain associated with the cool burn signal, and thus the panelist did not rate the products with high menthol too much higher on cool burn sensation, until the activation of the potassium channel subsided at and beyond 10 minutes after use.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care composition comprising a TREK-1 agonist; wherein the TREK-1 agonist is Dioctyl Adipate and wherein the TREK-1 agonist is present in an amount of from about 0.01% to about 0.8% based on the total weight of the personal care composition.

2. The personal care composition of claim 1 wherein the personal care composition is an oral care composition.

3. The personal care composition of claim 2, wherein the oral care composition is an oral care strip comprising a strip of material and an oral care substance.

4. The personal care composition of claim 3, wherein the TREK-1 agonist is present in the oral care substance.

5. The personal care composition of claim 4, wherein the oral care substance comprises at least one of oxalic acid, potassium salts of oxalic acid, hydrogen peroxide, carbamide peroxide, sodium fluoride, sodium monofluorophosphate, pyrophosphate, chlorhexidine, polyphosphate, triclosan, or enzymes.

6. A method for measuring TREK-1 potassium channel activation comprising:
   a) providing oral care composition having from about 0.01% to about 0.8% TREK-1 agonist;
   b) applying pain stimuli to oral tissues;
   c) treating oral tissues with oral care composition; and
   d) measuring the reduction in perceived pain;
   wherein the measuring was done using cells transfected with a TREK-1 receptor sequence and wherein the TREK-1 agonist is Dioctyl Adipate.

7. The method of claim 6, wherein the treatment comprises application of an oral care strip comprising a strip of material and an oral care substance.

8. The method of claim 7, wherein the TREK-1 agonist is present in the oral care substance.

9. The method of claim 8, wherein the oral care substance comprises at least one of oxalic acid, potassium salts of oxalic acid, hydrogen peroxide, carbamide peroxide, sodium fluoride, sodium monofluorophosphate, pyrophosphate, chlorhexidine, polyphosphate, triclosan, or enzymes.

10. The method of claim 6, wherein the oral care composition comprises at least one of potassium salts, stannous fluoride, salicyl alcohol, benzocaine, dyclonine hydrochloride, hexylresorcinol, menthol, alum, zinc chloride, elm bark, gelatin, glycerin, pectin, carbamide peroxide, hydrogen peroxide, sodium bicarbonate, or sodium perborate.

11. The method of claim 10, wherein the potassium salt is at least one of potassium nitrate or potassium oxalate.

12. The method of claim 6, wherein the TREK-1 receptor sequence has at least about 70% sequence identity with SEQ ID NO: 1.

* * * * *